(12) United States Patent
Madabhushi et al.

(10) Patent No.: US 11,817,204 B2
(45) Date of Patent: Nov. 14, 2023

(54) SPECIALIZED COMPUTER-AIDED DIAGNOSIS AND DISEASE CHARACTERIZATION WITH A MULTI-FOCAL ENSEMBLE OF CONVOLUTIONAL NEURAL NETWORKS

(71) Applicant: Case Western Reserve University, Cleveland, OH (US)

(72) Inventors: Anant Madabhushi, Shaker Heights, OH (US); Nathaniel Braman, Bethel Park, PA (US); Tristan Maidment, Cleveland, OH (US); Yijiang Chen, Cleveland, OH (US)

(73) Assignees: Case Western Reserve University, Cleveland, OH (US); The United States Government as Represented by The Department of Veteran Affairs, Washington, DC (US)

( * ) Notice: Subject to any disclaimer, the term of this patent is extended or adjusted under 35 U.S.C. 154(b) by 309 days.

(21) Appl. No.: 17/116,366

(22) Filed: Dec. 9, 2020

(65) Prior Publication Data
US 2021/0174504 A1 Jun. 10, 2021

Related U.S. Application Data

(60) Provisional application No. 62/945,327, filed on Dec. 9, 2019.

(51) Int. Cl.
*G16H 30/40* (2018.01)
*G06T 7/00* (2017.01)
(Continued)

(52) U.S. Cl.
CPC ............ *G16H 30/40* (2018.01); *A61B 6/025* (2013.01); *A61B 6/469* (2013.01); *A61B 6/502* (2013.01);
(Continued)

(58) Field of Classification Search
CPC ................ G06T 7/0012; G06T 7/11; G06T 2207/10112; G06T 2207/20081;
(Continued)

(56) References Cited

U.S. PATENT DOCUMENTS

| | | | | | |
|---|---|---|---|---|---|
| 5,984,870 | A | * | 11/1999 | Giger | ................. G06T 7/0012 600/443 |
| 2006/0120608 | A1 | * | 6/2006 | Luo | ..................... G06T 7/0012 382/224 |

(Continued)

OTHER PUBLICATIONS

Geras, Krzysztof J et al. "High-Resolution Breast Cancer Screening with Multi-View Deep Convolutional Neural Networks." ArXiv abs/1703.07047 (2017): n. pag. (Year: 2017).*

*Primary Examiner* — Amandeep Saini
*Assistant Examiner* — Julius Chai
(74) *Attorney, Agent, or Firm* — Eschweiler & Potashnik, LLC

(57) ABSTRACT

Embodiments discussed herein facilitate determination of whether lesions are benign or malignant. One example embodiment is a method, comprising: accessing medical imaging scan(s) that are each associated with distinct angle(s) and each comprise a segmented region of interest (ROI) of that medical imaging scan comprising a lesion associated with a first region and a second region; providing the first region(s) of the medical imaging scan(s) to trained first deep learning (DL) model(s) of an ensemble and the second region(s) of the medical imaging scan(s) to trained second DL model(s) of the ensemble; and receiving, from the ensemble of DL models, an indication of whether the lesion is a benign architectural distortion (AD) or a malignant AD.

26 Claims, 10 Drawing Sheets

(51) Int. Cl.
*A61B 6/00* (2006.01)
*A61B 6/02* (2006.01)
*G16H 50/20* (2018.01)
*G06N 3/04* (2023.01)
*G06T 7/11* (2017.01)
*G06F 18/214* (2023.01)
*G06V 10/25* (2022.01)
*G06V 10/764* (2022.01)
*G06V 10/82* (2022.01)

(52) U.S. Cl.
CPC .......... *A61B 6/5217* (2013.01); *G06F 18/214* (2023.01); *G06N 3/04* (2013.01); *G06T 7/0012* (2013.01); *G06T 7/11* (2017.01); *G06V 10/25* (2022.01); *G06V 10/764* (2022.01); *G06V 10/82* (2022.01); *G16H 50/20* (2018.01); *G06T 2207/10112* (2013.01); *G06T 2207/20081* (2013.01); *G06T 2207/20084* (2013.01); *G06T 2207/30068* (2013.01); *G06T 2207/30096* (2013.01); *G06V 2201/03* (2022.01)

(58) Field of Classification Search
CPC . G06T 2207/20084; G06T 2207/30068; G06T 2207/30096; G16H 50/20; G16H 30/40; A61B 6/025; A61B 6/469; A61B 6/502; A61B 6/5217; G06K 9/6256; G06N 3/04; G06V 2201/03
See application file for complete search history.

(56) References Cited

U.S. PATENT DOCUMENTS

| | | | |
|---|---|---|---|
| 2010/0063948 A1* | 3/2010 | Virkar | G06N 20/10 707/769 |
| 2017/0071562 A1* | 3/2017 | Suzuki | A61B 6/025 |
| 2017/0116536 A1* | 4/2017 | Hardjasa | G06N 3/08 |
| 2019/0130562 A1* | 5/2019 | Liu | G06F 18/2414 |
| 2020/0395123 A1* | 12/2020 | Akselrod-Ballin | G06N 3/08 |
| 2021/0019599 A1* | 1/2021 | Mazzawi | G06N 3/086 |
| 2021/0056717 A1* | 2/2021 | Ranganathan | G06T 7/337 |
| 2021/0225027 A1* | 7/2021 | Wang | G06T 7/73 |
| 2021/0350187 A1* | 11/2021 | Hu | G16H 30/40 |

\* cited by examiner

| Number and Layer Type (from left to right) | Details |
|---|---|
| 3 x 3D Convolutional | 3x3x3 Kernel Size, TanH Activation |
| 1 x 3D Convolutional | 2x2x2 Kernel Size, ReLu Activation |
| 4 x 2D Convolutional | 3x3 Kernel Size, ReLu Activation |
| 4 x Dense | ReLu Activation |
| 1 x Dense | Sigmoid Activation, Output |

| Spatial Weighting | Acquisitional View | AUC | Sensitivity | Specificity |
|---|---|---|---|---|
| Intralesional | Intralesional, CC | 0.65 | 0.80 | 0.50 |
| Perilesional | Perilesional, CC | 0.51 | 0.40 | 0.40 |
| Intralesional | Intralesional, ML | 0.49 | 0.60 | 0.46 |
| Perilesional | Perilesional, ML | 0.55 | 0.60 | 0.43 |
| Combined Ensemble | Combined Ensemble | 0.72 | 1.0 | 0.6 |

FIG. 5

| Region | View | AUC | Sensitivity | Specificity |
|---|---|---|---|---|
| Intralesional | CC | 0.65 | 0.80 | 0.50 |
| Perilesional | CC | 0.51 | 0.40 | 0.40 |
| Intralesional | ML | 0.49 | 0.60 | 0.46 |
| Perilesional | ML | 0.55 | 0.60 | 0.43 |
| Combined | N/A | 0.80 | 0.60 | 1.0 |

FIG. 9

SPECIALIZED COMPUTER-AIDED DIAGNOSIS AND DISEASE CHARACTERIZATION WITH A MULTI-FOCAL ENSEMBLE OF CONVOLUTIONAL NEURAL NETWORKS

CROSS REFERENCE TO RELATED APPLICATIONS

This application claims the benefit of U.S. Provisional Patent Application No. 62/945,327 filed Dec. 9, 2019, entitled "SPECIALIZED COMPUTER-AIDED DIAGNOSIS AND DISEASE CHARACTERIZATION WITH A MULTI-FOCAL ENSEMBLE OF CONVOLUTIONAL NEURAL NETWORKS", the contents of which are herein incorporated by reference in their entirety.

FEDERAL FUNDING NOTICE

This invention was made with government support under grants CA221383, CA199374, CA202752, CA208236, CA216579, CA220581, CA233216, EB007509, and RR012463 awarded by the National Institutes of Health; grant(s) IBX004121A awarded by the United States Department of Veterans Affairs; and grants W81XWH-15-1-0558, W81XWH-18-1-0440, and W81XWH-16-1-0329 awarded by the Department of Defense. The government has certain rights in the invention.

BACKGROUND

3D Digital Breast Tomosynthesis (DBT) offers greater sensitivity than 2D mammography to the presence of architectural distortions (AD). Radial Scars (RS) are a benign AD presentation that are visually indistinguishable from malignant AD. Deep learning methods have shown potential to enhance the accuracy of general breast cancer diagnoses, but struggle with challenging diagnoses.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 5 illustrates a chart describing the various networks the comprise the ensemble, and their individual performances on the independent test set, in connection with various aspects discussed herein.

FIG. 9 illustrates a chart of metrics used to evaluate diagnostic performance of the individual networks and the combined ensemble classifier, in connection with various aspects discussed herein.

DETAILED DESCRIPTION

Figure 1:
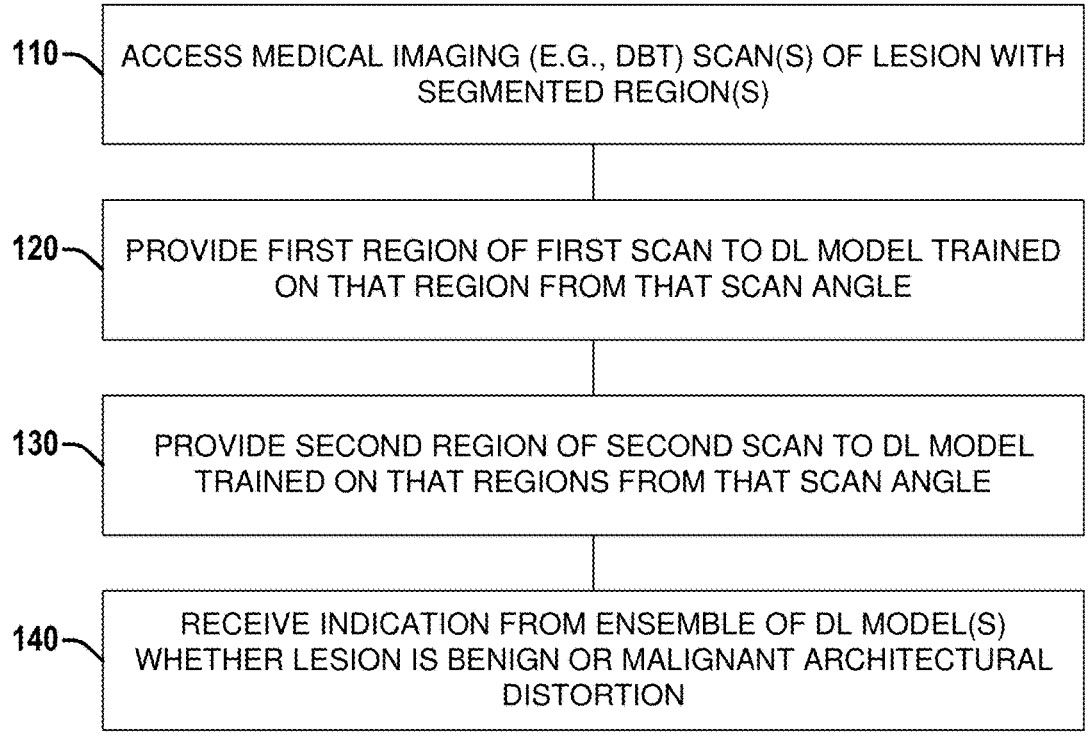
FIG. 1 illustrates a flow diagram of an example method/set of operations that can be performed by one or more processors to determine whether an architectural distortion (AD) on a medical imaging scan (e.g., 3D Digital Breast Tomography (DBT), etc.) is benign or malignant, according to various aspects discussed herein.

Various embodiments discussed herein can construct and/or employ an ensemble of Deep Learning (DL) models to determine whether an architectural distortion (AD) on a medical imaging scan (e.g., 3D DBT) is benign or malignant.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Embodiments include apparatus, systems, operations, methods, or other embodiments that can construct or employ an ensemble of deep learning (e.g., Convolutional Neural Network (CNN)) models to determine whether an architectural distortion (AD) on a medical imaging scan (e.g., 3D DBT) is benign or malignant. Different DL models of the ensemble can be trained on different combinations of view (e.g., craniocaudal, mediolateral, etc.) and region (e.g., intralesional, perilesional), such that the combined ensemble can provide improved ability to determine whether the lesion is a benign or malignant AD.

Referring to FIG. 1, illustrated is a flow diagram of an example method/set of operations 100 that can be performed by one or more processors to determine whether an architectural distortion (AD) on a medical imaging scan (e.g., 3D Digital Breast Tomography (DBT), etc.) is benign or malignant, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, accessing one or more medical imaging (e.g., 3D DBT) scans, wherein each medical imaging scan of the one or more medical imaging scans is associated with a distinct angle, wherein each medical imaging scan of the one or more medical imaging scans comprises a segmented region of interest (ROI) of that medical imaging scan comprising a lesion, wherein the segmented ROI of that medical imaging scan comprises one or more regions associated with that lesion. In various embodiments and in the example use case discussed below, the imaging scan(s) can be obtained via a system and/or apparatus implementing the set of operations 100, or can be obtained from a separate medical imaging system. Additionally, the imaging scan(s) can be accessed contemporaneously with or at any point prior to performing the set of operations 100.

The set of operations 100 can further comprise, at 120, providing a first region of the one or more regions of a first medical imaging scan of the one or more medical imaging scans to a first deep learning (DL) model of an ensemble of DL models, wherein the first DL model is trained on the first region and the distinct angle of the first medical imaging scan.

The set of operations 100 can further comprise, at 130, providing a second region of the one or more regions of a second medical imaging scan of the one or more medical imaging scans to a second DL model of the ensemble, wherein the second DL model is trained on the second region and the distinct angle of the second medical imaging scan, and wherein at least one of the first region is different from the second region or the first medical imaging scan is different from the second medical imaging scan.

The set of operations 100 can further comprise, at 140, receiving, from the ensemble of DL models, an indication of whether the lesion is a benign architectural distortion (AD) or a malignant AD.

Additionally, or alternatively, set of operations 100 can comprise one or more other actions discussed herein in connection with determining whether a lesion is a benign or malignant architectural distortion (AD).

Figure 2:
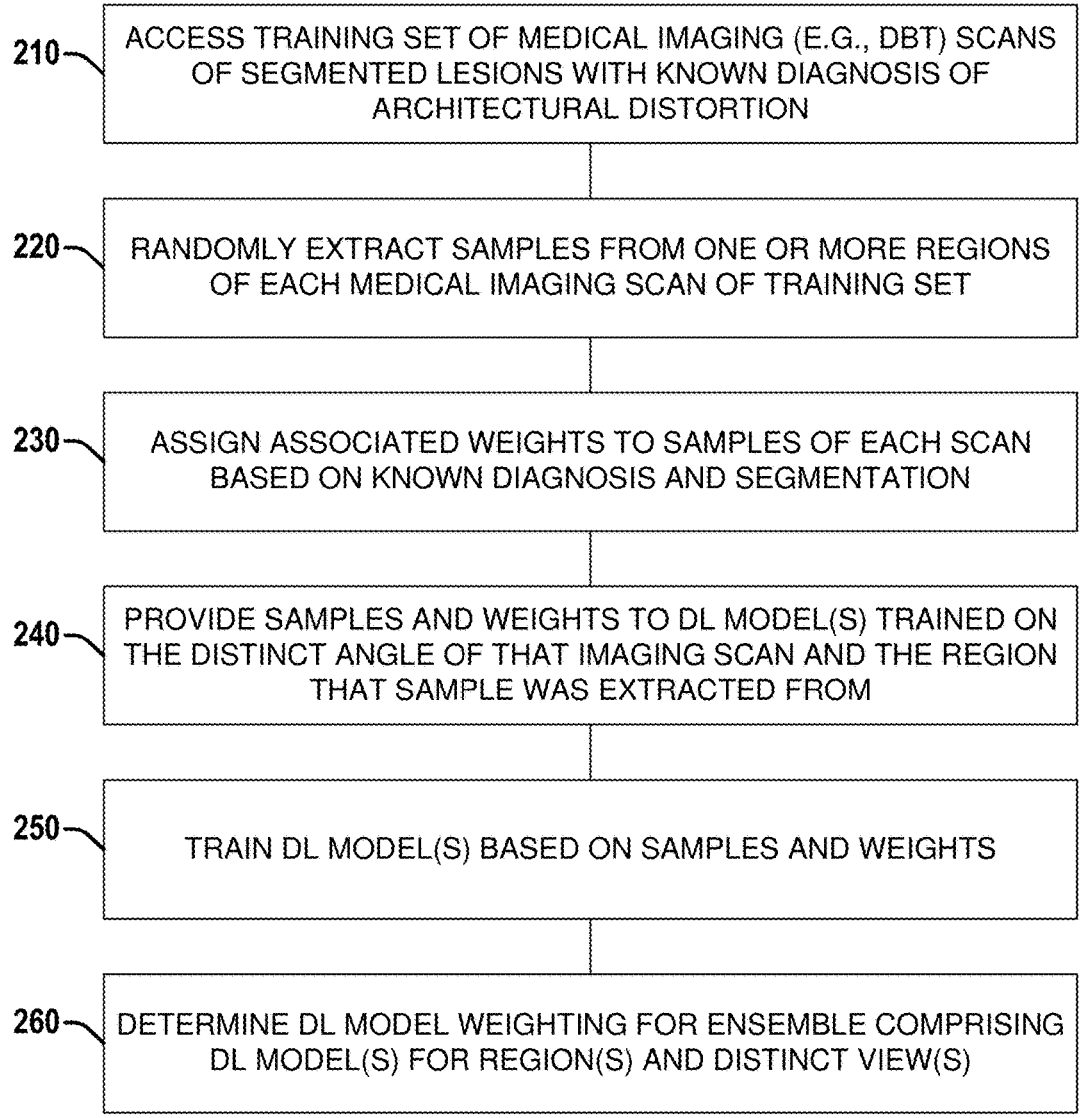
FIG. 2 illustrates a flow diagram of an example method/set of operations that can be performed by one or more processors to construct a model to determine whether an AD on a medical imaging scan (e.g., 3D DBT, etc.) is benign or malignant, in connection with various aspects discussed herein.

Referring to FIG. 2, illustrated is a flow diagram of an example method/set of operations 200 that can be performed by one or more processors to construct a model to determine whether an architectural distortion (AD) on a medical imaging scan (e.g., 3D Digital Breast Tomography (DBT), etc.) is benign or malignant, in connection with various aspects discussed herein.

The set of operations 200 can comprise, at 210, accessing a training set comprising, for each patient of a plurality of patients, one or more medical imaging scans of that patient, wherein each medical imaging scan of the one or more medical imaging scans is associated with a distinct angle, wherein each medical imaging scan of the one or more medical imaging scans of that patient comprises a segmented region of interest (ROI) of that medical imaging scan comprising a lesion of that patient, wherein the segmented ROI of that medical imaging scan comprises a first region of that medical imaging scan associated with the legion of that patient and a second region of that medical imaging scan associated with the lesion of that patient, and wherein the lesion of that patient is associated with a known diagnosis for that patient. In various embodiments and in the example use case discussed below, the imaging scans can be obtained via a system and/or apparatus implementing the set of operations 200, or can be obtained from a separate medical imaging system (e.g., MRI system). Additionally, the imaging scans can be accessed contemporaneously with or at any point prior to performing the set of operations 200.

The set of operations 200 can further comprise, at 220, for each medical imaging scan of the training set, randomly extracting one or more associated first samples from the first region of that medical imaging scan and one or more associated second samples from the second region of that medical imaging scan.

The set of operations 200 can further comprise, at 230, for each medical imaging scan of the training set, assigning an associated weight to each associated first sample of the one or more associated first samples and to each associated second sample of the one or more associated second samples based at least in part on the known diagnosis for that patient.

The set of operations 200 can further comprise, at 240, for each medical imaging scan of the training set, providing the one or more associated first samples of that medical imaging scan and their associated weights to an associated first Deep Learning (DL) model for the distinct view of that medical imaging scan, and providing the one or more associated second samples of that medical imaging scan and their associated weights to an associated second DL model for the distinct view of that medical imaging scan.

The set of operations 200 can further comprise, at 250, for each medical imaging scan of the training set, training the associated first DL model for the distinct view of that medical imaging scan based on the one or more associated first samples of that medical imaging scan and their associated weights, and training the associated second DL model for the distinct view of that medical imaging scan based on the one or more associated second samples of that medical imaging scan and their associated weights.

The set of operations 200 can further comprise, at 260, determining an associated DL model weighting for each DL model of an ensemble of DL models comprising the first DL for the distinct view of each medical imaging scan and the second DL model for the distinct view of each medical imaging scan.

Additionally, or alternatively, set of operations 200 can comprise one or more other actions discussed herein in connection with constructing a model to determine whether an architectural distortion (AD) on medical imaging scan(s) (e.g., 3D Digital Breast Tomography (DBT), etc.) is benign or malignant.

Additional aspects and embodiments are discussed below in connection with the following example use case.

Example Use Case 1: Normal Sampling Ensemble Architecture for Rare Visual Confounders in Breast Tomosynthesis The following discussion provides example embodiments in connection with a first example use case involving using deep learning to distinguish benign and malignant architectural distortions (AD) in 3D digital breast tomosynthesis.

Overview

Purpose: Complex sclerosing lesions and radial scars are rare benign architectural distortions (AD), which present a difficult diagnostic problem due to the visual similarity they share with malignant AD; practice standards state that patients found to have AD should be biopsied. 3D digital breast tomosynthesis (DBT) has shown improved cancer detection and lower recall rate compared to traditional 2D digital mammography, as well as greater sensitivity to the presence of AD. Computer-aided diagnosis systems (CAD) can alleviate unnecessary biopsies through Deep Learning (DL) approaches, involving the training of a convolutional neural network to recognize disease patterns. These approaches are tailored to general screening settings and struggle with rare and challenging confounders, such as distinguishing benign radial scar from visually similar malignancy. An ensemble of purpose-built DL classifiers, trained on randomly sampled and differentially weighted regions of AD, will provide means to differentiating malignant and benign AD.

Materials and Methods: A dataset consisting of 69 patients (27 benign; 42 malignant) was collected, each with multiple digital breast tomosynthesis (DBT) exams. 49 had lesions visible in the mediolateral oblique (MLO) view, 23 had lesions in the ML (mediolateral) view, and 68 had lesions visible in the craniocaudal (CC) view, resulting in a total of 140 DBT volumes. All lesions and surrounding AD were annotated by a radiologist with a circular region-of-interest (ROI) on the slice. 3D patches of size 24×24×12 pixels were extracted randomly within the ROI of each view. These samples were separately weighted for perilesional and interlesional analysis, with respect to distance from center of the lesion. An ensemble of DL classifiers was trained, each classifier having a unique combination of lesion view and focus. The classifiers provide two predictions, one consisting of the patch prediction majority and the other a patch-wise confidence estimate aggregation. Cases were trained using cross validation, and the best classifier tested on a held out independent validation set.

Results: The best ensemble achieved an area under the receiver operating curve (AUC) of 0.688 within cross validation training. This ensemble, making case predictions on the independent validation set, achieved an area under the receiver operating curve (AUC) of 0.72, a sensitivity of 1.0 and specificity of 0.6. This indicates the proposed DL ensemble classifier would decrease the number of unnecessary biopsies without incorrectly classifying malignant lesions. An ensemble comprising all of the classifiers generated during cross-validation training, when tested on the independent validation set, achieved an AUC of 0.8, specificity of 1.0, and sensitivity of 0.6, resulting in a case accuracy of 82%.

Conclusion: A sample-based deep learning approach utilizing an ensemble of predictions from independent convolutional neural networks was effective in distinguishing confounding AD in 3D DBT, potentially reducing unnecessary biopsies.

Introduction

Deep Learning (DL) approaches for classification in medical imaging, involving the training of a convolutional neural networks (CNN) for pattern recognition tasks, are among the most promising means for the development of computer-aided diagnosis (CAD) platforms across a number of diagnostic modalities. The performance of such approaches is traditionally dependent upon large, annotated datasets to learn a diagnostic function in a generalizable fashion. Curation and annotation of datasets that are of sufficient size for training a deep model requires extensive time and resource and are accrued retrospectively from a general population based on availability. Rare confounders and more ambiguous diagnoses are therefore under-represented and are therefore not suited for conventional machine learning (ML) approaches, despite their special need for CAD confirmation.

One potential solution to this problem is to train a deep learning classifier dedicated for difficult and underrepresented diagnostic scenarios. In targeting a specialized sub-diagnosis corresponding to an uncommon presentation, the size of the dataset available for training will, by necessity, be limited. Furthermore, rare confounders often have complex presentations and ill-defined boundaries, making them challenging to annotate definitively, and difficult for a model to differentiate. Thus, automating diagnoses from visually similar malignancy means training a neural network for an intricate and multifaceted pattern recognition task given a limited and ambiguously labeled training corpus.

Ensemble learning has facilitated improvement in ML by combining the predictions of multiple weak ML classifiers into one superior classifier. The integration of multiple learners allows ensembles to address multiple hypotheses simultaneously, providing better predictive performance, greater generalizability, and higher resistance to noise. A crucial element in constructing a reliable ensemble is independence between the weak learners. The unique sources of variance presented by each weak classifier is minimized through ensemble voting. Furthermore, prediction performance is improved through the implicit diversity in independent weak classifiers.

The Digital Breast Tomosynthesis (DBT) diagnostic imaging modality generates a three-dimensional reconstruction of internal structures, offering improved cancer detection rate and lower recall rate relative to 2D digital mammography. The volumetric data provided by DBT allows for structural analysis of breast tissue, which provides means to find high-dimensional indicators for diagnosis.

Complex sclerosing lesions and radial scars are rare benign architectural distortions (AD). They present a difficult diagnostic problem due to the visual similarity they share with malignant AD (MAD), such as scirrhous carcinoma. Current practices require patients found to have masses resembling radial scar should be biopsied.

Materials and Methods

The experimental data was acquired via an Institutional Review Board approved, HIPAA compliant protocol. The dataset comprised of 69 patients with AD, each classified via biopsy (42 malignant, 27 benign). Each patient has a CC and either an MLO or ML tomographic projection. Patients were randomly divided into 5 different folds; each cohort maintained the same approximate distribution of malignant to benign. The first 4 folds were used for training and tuning via cross-validation, and the last cohort was held out to be used as an independent test set.

All data was acquired at the same site; images were obtained from a Sectra Medical tomography workstation. The patient data comprised a reconstructed volumetric tomogram and an elliptical segmentation, highlighting the AD. These elliptical segmentations were done by a resident at the data site, who had full access to the projections and medical diagnosis. The segmentations surround the region containing the AD and are associated with the specific slice in the reconstruction where the AD is most present.

Data limitations place emphasis on techniques such as patch sampling methods, which provide robust data augmentation by sampling with replacement. An unconventional sampling methodology was devised to further capitalize upon segmentation attributes. Given the radial nature of the lesion presentation, a new feature can be engineered which corresponds directly with the progression of the disease. The elliptical segmentation is used to approximate a 2D normal gaussian curve around the center of the lesion. The random samples pulled from inside the lesion are assigned a weight, corresponding to the probability defined by the distribution, allowing for a more concise way of defining the disease. Traditional binary classification requires the assumption that all examples are entirely benign or malignant. While ground truth labels, such as those obtained via biopsy, are binary, not all data contained in an image is binary. The boundaries of the radial scar structure cannot be easily annotated by clinicians due to discrepancies in defining the boundary of the lesion. As such, certain portions of the image may contain data that is neither positive (scirrhous carcinoma) or negative (radial scar); it may be healthy normal tissue. Since the exact segmentations for the lesions are difficult to define due to the textural complexity of the lesions, this probabilistic representation more accurately represents the lesions.

The defined methodology maximizes ensemble performance by compounding information from multiple data sources. This process restrains the possible sources of data variance, improving the classification performance. The example patients with AD were screened at two view angles, Cranial-Caudal (CC) and Medio-Lateral Oblique (MLO), providing two independently obtained representations of the lesions. Using these multiple projections available in the dataset, the multiple independently obtained data representations of each example were utilized by assigning a classifier to each view.

To further maximize weak classifier independence, learners were isolated to specific regions of the lesion. The probabilistic maps provided by radial distance metric defines means for separating weak classifiers to different regions. This spatial focus can be mandated by isolating textures from the perilesional region for one learner, and intralesional regions for another. Previous studies show this improves diagnostic performance.

Experimental Design

The (n=69) patients were randomly divided into 5 different cohorts; each cohort maintained approximately the same distribution of malignant to benign. The first four cohorts were used for training and testing, the last saved for validation. All image data was normalized between [0, 1] prior to sampling. A total of 2048 samples, each of size (48×48×8), were acquired from each cohort. Benign and Malignant sample distributions within each cohort were equally balanced to avoid bias induced by skewed classes. The samples were randomly picked selected from the tomograms, with replacement, from all available cases within each cohort.

Figure 3:
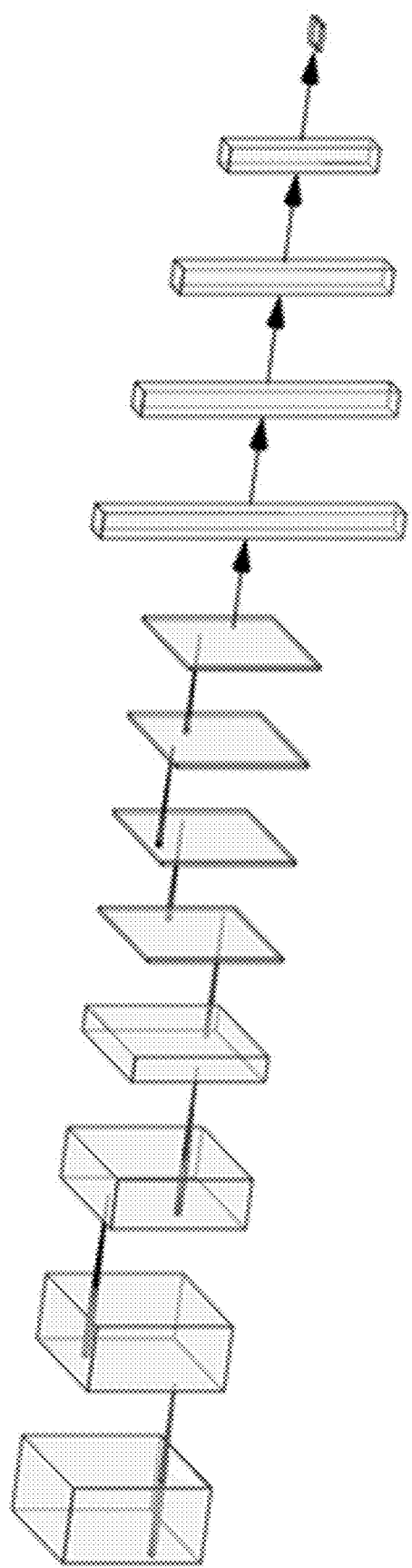
FIG. 3 illustrates a visual representation of the 3D CNN structure of each weak classifier in the ensemble, and a detailed chart containing layer information, in connection with various aspects discussed herein.

The ensemble was composed of weak classifiers, each with a spatial weighting, intralesional or perilesional, and a specific view, CC or MLO. The network structure used for this problem utilizes 4 convolutional layers, the last with max pooling, followed by three dense layers. Kernels were volumetric and of size (3×3×3) throughout all convolutional layers. Batch-normalization provided significant improvements in weak learner cross-validation performance. Referring to FIG. 3, illustrated is a visual representation of the 3D CNN structure of each weak classifier in the ensemble, and a detailed chart containing layer information, in connection with various aspects discussed herein.

Figure 4:
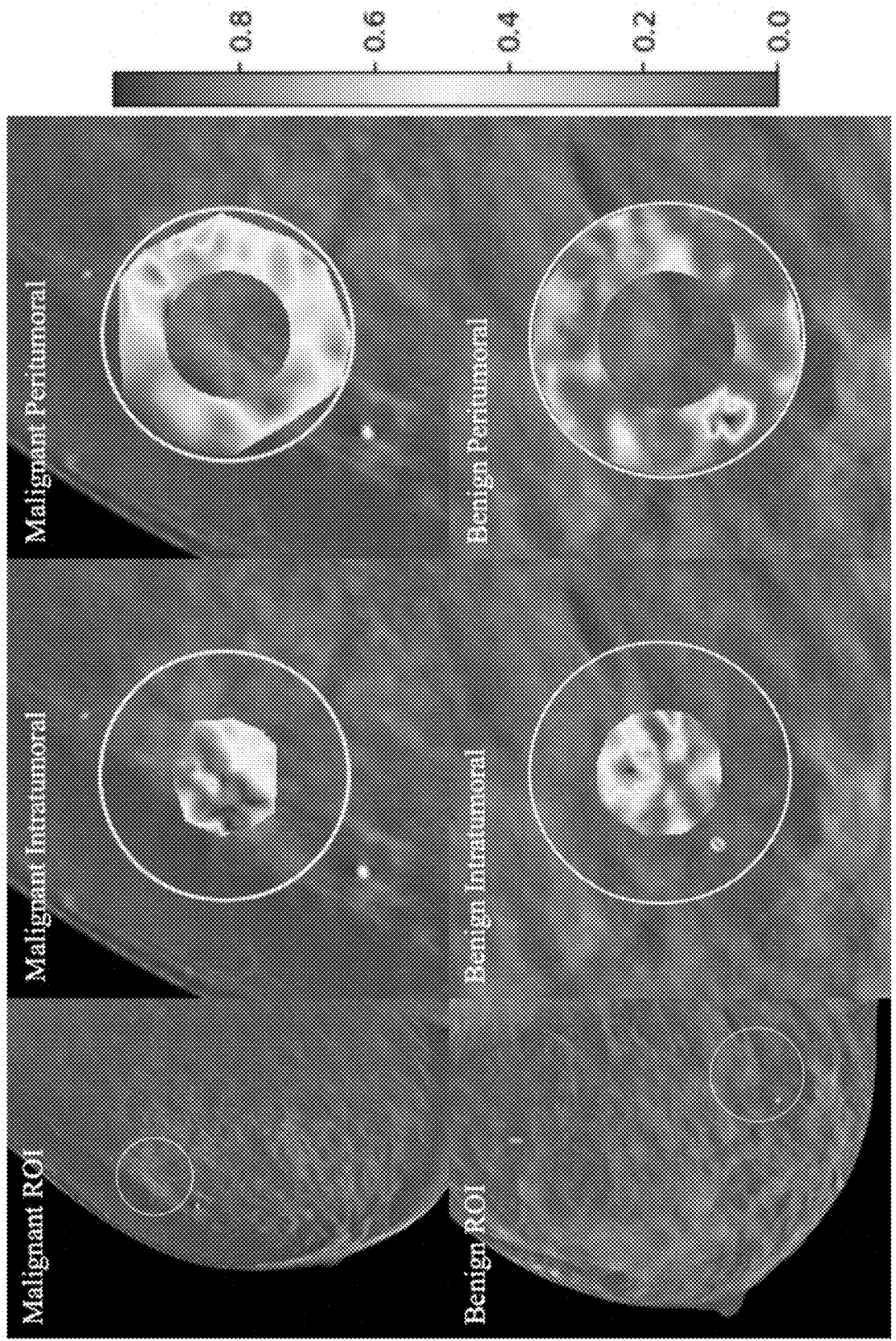
FIG. 4 illustrates example images showing interpolated visual prediction probability maps of both a malignant and benign AD. The white ring demonstrates the radial ROI defined by the radiologist, in connection with various aspects discussed herein.

Referring to FIG. 4, illustrated are example images showing interpolated visual prediction probability maps of both a malignant and benign AD. The white ring demonstrates the radial ROI defined by the radiologist, in connection with various aspects discussed herein. The texture maps describe prediction output, with output value correlating with malignancy likelihood. The second column depicts predictions made by intralesional networks, the third depicts predictions from perilesional networks.

The ensemble comprised four weak neural networks, each with a unique combination of spatial weighting and view. These networks, as an ensemble, are trained with cross validation (CV), within the first four cohorts. The ensemble that performed the best in CV was evaluated on the testing data, cohort 5.

Results

The best ensemble was determined via cross validation between cohorts 1-3, internally achieving a case accuracy of 61.5% and an AUC of 0.688. This ensemble was then evaluated on the independent validation dataset. The ensemble's performance was tested on the validation dataset. Referring to FIG. 5, illustrated is a chart describing the various networks the comprise the ensemble, and their individual performances on the independent test set, in connection with various aspects discussed herein. Furthermore, FIG. 4 also indicates the final ensemble performance on the independent test set.

Figure 6:
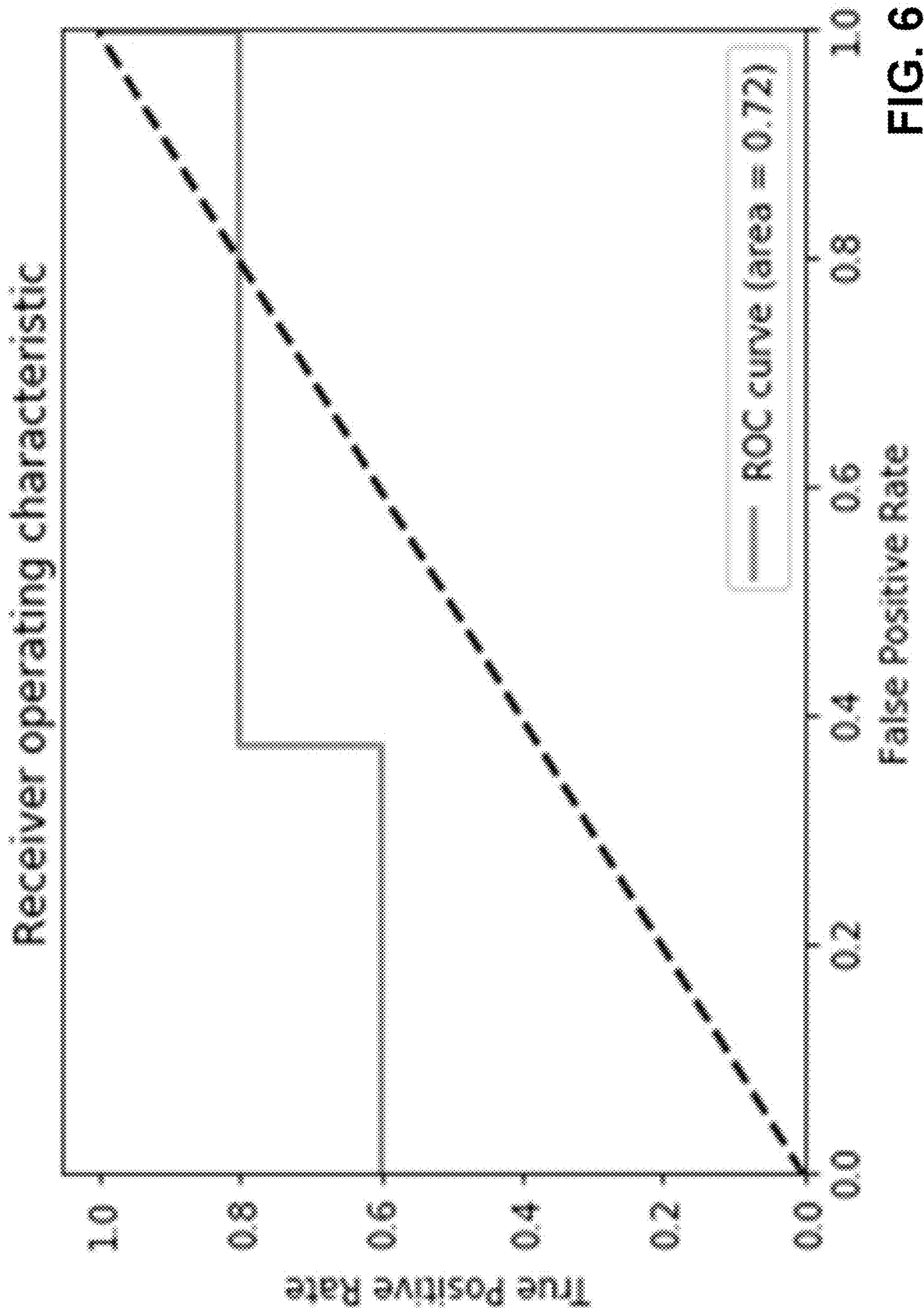
FIG. 6 illustrates a receiver operating characteristic (ROC) curve for the best combined ensemble, in connection with various aspects discussed herein.

Referring to FIG. 6, illustrated is a receiver operating characteristic (ROC) curve for the best combined ensemble, in connection with various aspects discussed herein. The ensemble ROC depicts a peak sensitivity of 1.0, thereby not predicting any patients incorrectly benign. Furthermore, even at this high sensitivity, the model maintained a specificity of 0.6. The networks trained to recognize patterns of malignancy at the intralesional region of the distortion outperformed the perilesional-focused networks. Furthermore, the CC view was found to be the most discriminating in independent test set assessment.

Discussion

FIG. 6 provides clear evidence that the ensemble, with its specially defined weak classifiers, can provide predictions that aid diagnosis. Most notably, the ensemble was able diagnose all patients with benign AD correctly on the validation data, a sensitivity of 1.0, while maintaining a specificity of 0.6. Given the visual similarities between malignant and benign AD, this tool provides a means for reducing the number of unnecessary biopsies.

The performance of the ensemble of the first example use case was not without limitations. First, common to most computer aided diagnosis work, the reproducibility of these methods at other data sites is currently unknown, meaning the utility provided by this tool may be limited to our geographical region. Second, there are certain requirements that must be fulfilled in order to use this tool. Each patient with AD to be diagnosed by this tool must have two tomograms, one from CC and one from MLO. The first example use case demonstrated that accurate differentiation between benign and malignant AD is possible using both CC and MLO projections. It should be noted that as a retroactive analysis, current practices often acquire both projections, which indicates that this may not prove to be a barrier to entry. Furthermore, segmentations in the first example use case were done manually, to highlight the region of interest. Automatic segmentation can expedite this process, but was not explored in the first example use case.

The complexity of the CNN used in the first example use case was simple compared to popular deep learning structures, such as ResNet or YoloV3. The reasoning for this was two-fold. First, the network did not consider spatial data at a macroscopic level. This is because the network was responsible solely for patch-wise classification, not entire case prediction, relegating spatial inference to case prediction. Since higher complexity 3D CNNs capitalize upon volumetric data, generalizability can be achieved through a smaller network structure. Through testing, it was found that a moderately deep 3D CNN provided consistently stable results, specifically in cross validation. The complexity induced by the 3D CNN was further reduced by sampling along all axes, significantly increasing sample variability.

The different sized lesions were addressed via patch sampling, since scaling the volumes results in artifacts that may induce biases. Effective patch sampling was achieved via probabilistic weighting. Tests with binary patches were inconsistent, and often failed to generalize, even with significant hyperparameter tuning. This may be attributed to non-AD tissue contained in the samples located at the edges of the lesion, which would be represented in both the benign and malignant datasets. Probabilistic weighting may provide better generalization by decreasing the importance of such patches, which have a lower weight.

On the validation set, each network provided benefit to the ensemble, with the exception of the intralesional ML network. Although this network could potentially be omitted, since its performance could degrade the ensembles overall performance, this network had acceptable performance throughout training, and was included in validation to prevent external bias. It should be noted, however, that removing this weak classifier from the ensemble did not affect the final predictions on the validation set, confirming the efficacy and robustness of ensemble classifiers.

The third example use case demonstrated that computer aided diagnosis can effectively distinguish confounding AD in 3D DBT, potentially reducing unnecessary biopsies.

Example Use Case 2: a Combination of Intra- and Peri-Lesion Deep Learning Classifiers from Multiple Views Enables Accurate Diagnosis The following discussion provides example embodiments in connection with a second example use case involving using deep learning to distinguish benign and malignant architectural distortions (AD) in 3D digital breast tomosynthesis.

Overview

3D Digital Breast Tomosynthesis (DBT) offers greater sensitivity than 2D mammography to the presence of architectural distortions (AD). Radial Scars (RS) are a benign AD presentation that are visually indistinguishable from malignant AD. Deep learning methods have shown potential to enhance the accuracy of general breast cancer diagnoses, but struggle with challenging diagnoses. Two angles of the lesion are captured via CC and MLO views. View specific deep learning algorithms provide independent diagnostic indicators. Intralesional and perilesional regions have different visual manifestations and are analyzed separately.

Objectives

Experiment 1: Assess discrimination performance between benign and malignant AD for the view and region-specific deep learning classifiers.

Experiment 2: Evaluate if combining predictions from the view-specialized classifiers provides better case-level predictions than a single classifier.

Methods

Figure 7:
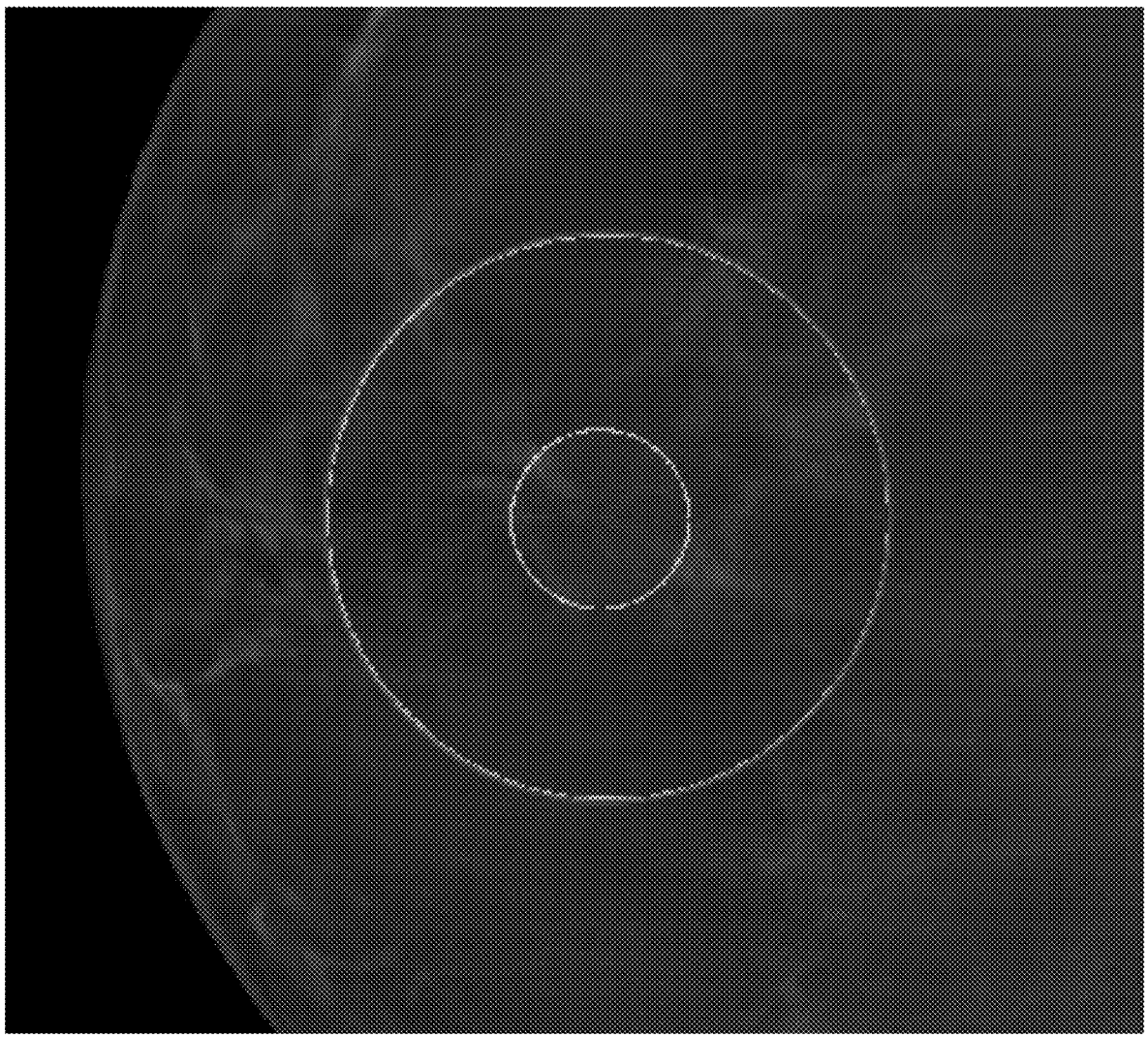
FIG. 7 illustrates an image showing an example AD overlaid with the annotated region of interest (ROI), in connection with various aspects discussed herein.

1—Data Preparation: Scans from 69 patients with AD visible in the CC and MLO DBT views were each annotated with an elliptical region of interest (ROI). 27 patients were diagnosed benign and 42 malignant, via biopsy. 56 patients were utilized for training and tuning, and 13 patients were held for testing. Structural samples of size 5 mm×5 mm×1 mm were extracted randomly with replacement from both regions. Referring to FIG. 7, illustrated is an image showing an example AD overlaid with the annotated region of interest (ROI), in connection with various aspects discussed herein. The red ring depicts the boundary of the perilesional region, and the white ring contains the intralesional region.

2—Deep Learning: Inspired by the biology of the disease, the lesion textures were split into intra- and peri-lesion regions for independent analysis. Volumetric Convolution Neural Networks (CNNs) were selected to classify the lesions structural information, provided by the DBTs. The predictions from the CNNs can be dynamically combined, with each providing unique information from the intra- or peri-lesion tissues and CC or MLO view.

3—Training and Validation: Each CNN was individually trained and then tuned via 4-fold internal cross-validation, on the training patients. Weighted predictions from each CNN were combined for diagnosis, to be tested on the testing patients. Performance was assessed via the following metrics: area under the receiver operating characteristic curve (AUC), sensitivity, specificity, and accuracy.

Figure 8:
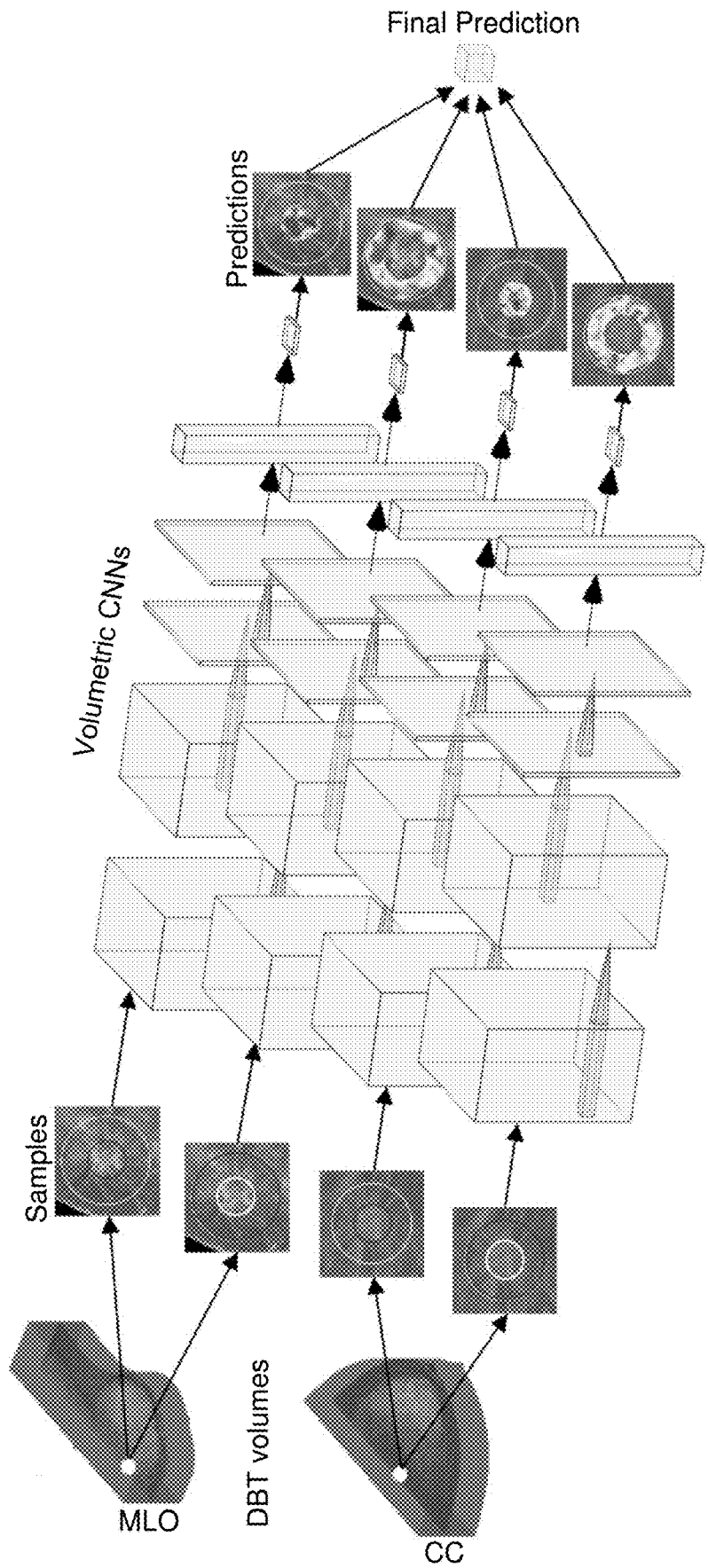
FIG. 8 illustrates a visual representation of the data pipeline of the second example use case, in connection with various aspects discussed herein.

Referring to FIG. 8, illustrated is a visual representation of the data pipeline of the second example use case, in connection with various aspects discussed herein. For each lesion, samples were extracted from randomly both views. Samples located from within the intralesional region were separated from the samples extracted from the perilesional region. Samples are individually predicted. A distinct volumetric 3D CNN structure was used for each combination of region (e.g., intralesional, perilesional) and imaging view (e.g., CC, MLO) to capture the structural information of these samples (although fewer layers are shown in FIG. 8 than FIG. 3 for ease of illustration, various embodiments can employ any CNNs as discussed herein for analysis of structural information by region (e.g., intralesional, perilesional) and imaging view (e.g., CC, MLO). Each sample output was weighted and aggregated for the final prediction.

Results

Experiment 1: View-specific CNNs learn different diagnostic indicators for AD diagnosis. Samples from the CC view were better than those from the ML view for identifying malignant AD, with an AUC=0.58±0.0049. Samples from the intralesional region marginally outperform the perilesional region, with an AUC=0.57±0.0064 vs AUC=0.53±0.0004. The specialized Intralesional and CC classifier outperformed the other classifiers. For comparison, a single neural network, trained on all patches and views, achieved an AUC=0.60. Referring again to FIG. 4, shown are Interpolated visual prediction probability maps of both a malignant and benign AD. The white ring demonstrates the radial ROI defined by the radiologist. The texture maps describe prediction output, with output value correlating with malignancy likelihood. The second column depicts predictions made by intralesional networks, and the third depicts predictions from perilesional networks.

Experiment 2: Combining predictions from multiple classifier predictions improves performance. The best ensemble performance of a single cross validation fold, when evaluated on the test patients, achieved an AUC=0.72. Referring to FIG. 9, illustrated is a chart of metrics used to evaluate diagnostic performance of the individual networks and the combined ensemble classifier, in connection with various aspects discussed herein. As shown in FIG. 9, the combined performance of all classifiers trained within cross-validation achieved an AUC=0.80.

Conclusions

The CC view was found to be the most discriminating in neural network assessment, and both lesion regions provide contribution different diagnostic information. The sample-based ensemble of specialized CNN classifiers was effective in distinguishing confounding AD in 3D DBT, potentially reducing the necessity of many biopsies.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing models to determine whether a lesion is a benign or malignant architectural distortion (AD) based at least in part on deep learned features or mappings that are not perceivable by the human eye, and involve computation that cannot be practically performed in the human mind. As one example, deep learning models as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 10:
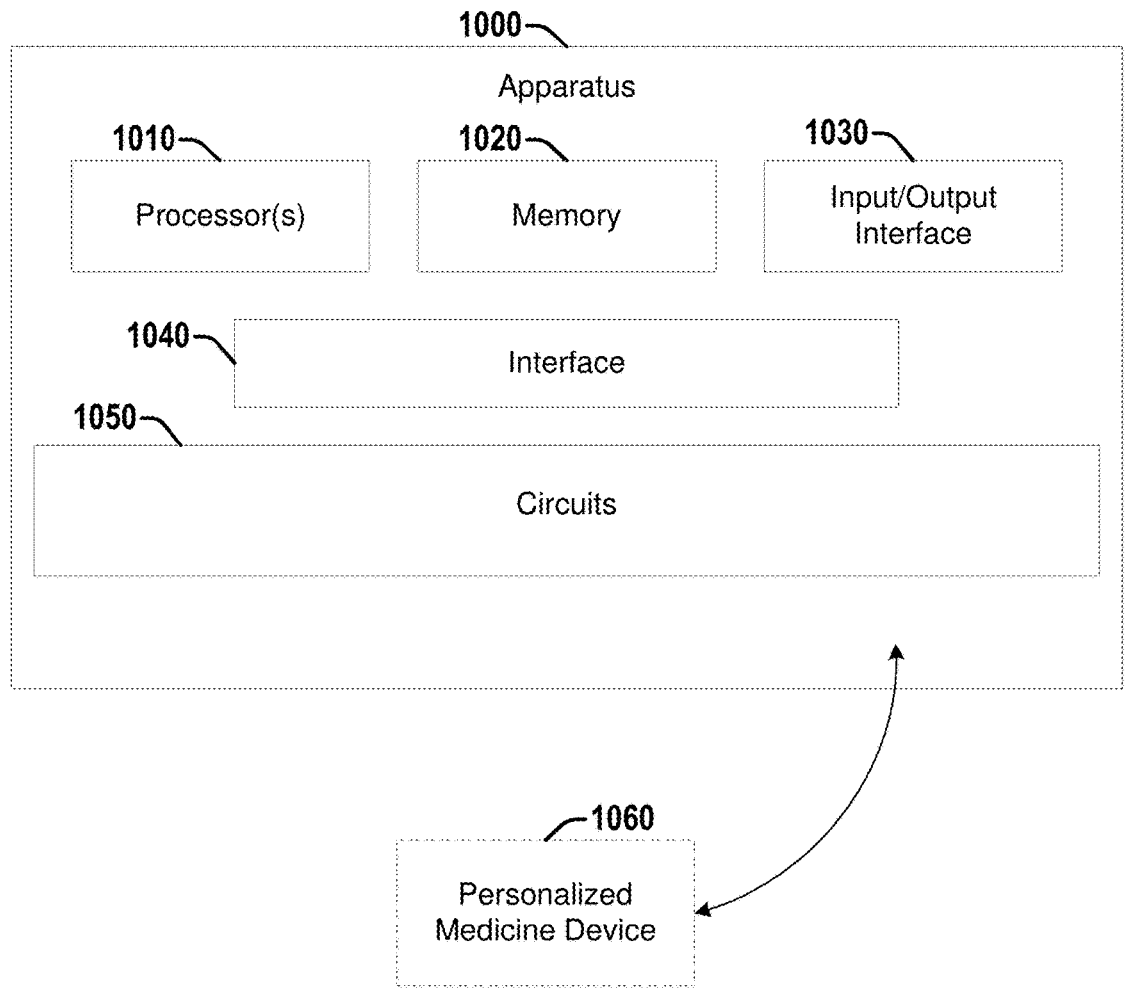
FIG. 10 illustrates a diagram of an example apparatus that can facilitate determination of whether an architectural distortion (AD) on a medical imaging scan (e.g., 3D Digital Breast Tomography (DBT), etc.) is benign or malignant and/or construct an ensemble of DL models to perform such a determination, according to various embodiments discussed herein.

Referring to FIG. 10, illustrated is a diagram of an example apparatus 800 that can facilitate determination of whether an AD on a medical imaging scan (e.g., 3D DBT, etc.) is benign or malignant and/or construct an ensemble of deep learning models to perform such a determination, according to various embodiments discussed herein. Apparatus 1000 can be configured to perform various techniques discussed herein, for example, various operations discussed in connection with sets of operations 100, 200, and/or other methods described herein. Apparatus 1000 can comprise one or more processors 1010 and memory 1020. Processor(s) 1010 can, in various embodiments, comprise circuitry such as, but not limited to, one or more single-core or multi-core processors. Processor(s) 1010 can include any combination of general-purpose processors and dedicated processors (e.g., graphics processors, application processors, etc.). The processor(s) can be coupled with and/or can comprise memory (e.g., of memory 1020) or storage and can be configured to execute instructions stored in the memory 1020 or storage to enable various apparatus, applications, or operating systems to perform operations and/or methods discussed herein. Memory 1020 can be configured to store one or more medical image volumes (e.g., obtained via 3D DBT, etc.) of a lesion (e.g., for training and/or determining whether an AD is benign or malignant). Each of the image(s) can comprise a plurality of pixels or voxels, each pixel or voxel having an associated intensity. Memory 1020 can be further configured to store additional data involved in performing operations discussed herein, such as for determining whether an AD is benign or malignant and/or training an ensemble of DL models to determine whether an AD is benign or malignant, as discussed in greater detail herein.

Apparatus 1000 can also comprise an input/output (I/O) interface 1030 (e.g., associated with one or more I/O devices), a set of circuits 1050, and an interface 1040 that connects the processor(s) 1010, the memory 1020, the I/O interface 1030, and the set of circuits 1050. I/O interface 1030 can be configured to transfer data between memory 1020, processor 1010, circuits 1050, and external devices, for example, medical imaging device(s) (e.g., 3D DBT, etc.), and/or one or more remote devices for receiving inputs and/or providing outputs to a clinician, patient, etc., such as optional personalized medicine device 1060.

The processor(s) 1010 and/or one or more circuits of the set of circuits 1050 can perform one or more acts associated with a method or set of operations discussed herein, such as set of operations 100, 200, etc. In various embodiments, different acts (e.g., different operations of a set of operations) can be performed by the same or different processor(s) 1010 and/or one or more circuits of the set of circuits 1050.

Apparatus 1000 can optionally further comprise personalized medicine device 1060. Apparatus 1000 can be configured to provide the prediction of whether the AD is benign or malignant and/or other data to personalized medicine device 1060. Personalized medicine device 1060 may be, for example, a computer assisted diagnosis (CADx) system or other type of personalized medicine device that can be used to facilitate monitoring and/or treatment of an associated medical condition. In some embodiments, processor(s) 1010 and/or one or more circuits of the set of circuits 1050 can be further configured to control personalized medicine device 1060 to display the determination of whether an architectural distortion (AD) on a medical imaging scan (e.g., 3D Digital Breast Tomography (DBT), etc.) is benign or malignant or other data on a computer monitor, a smartphone display, a tablet display, or other displays.

Additionally, while techniques discussed herein have been employed in specific contexts for employing an ensemble of deep learning (DL) models to classify lesions as benign or malignant based on a combination of two different view(s) and/or two different regions (e.g., an intralesional region and/or a perilesional region, etc.), techniques and embodiments discussed herein can be employed in a variety of other settings or scenarios to classify lesions as benign or malignant via an ensemble of deep learning (DL) models, each of which is trained on a specific combination of view and region, wherein each DL model of the ensemble differs from each other DL model of the ensemble with respect to one or both of view or region.

Examples herein can include subject matter such as an apparatus, a 3D DBT system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for determining whether an architectural distortion (AD) on a medical imaging scan (e.g., 3D Digital Breast Tomography (DBT), etc.) is benign or malignant, according to embodiments and examples described.

One embodiment includes a non-transitory computer-readable storage device storing computer-executable instructions that when executed control a processor to perform operations for training an ensemble architecture deep learning classifier, the operations comprising: accessing a dataset of digital breast tomosynthesis (DBT) exams, each DBT exam associated with a patient, where the dataset includes DBT exams associated with patients demonstrating benign architectural distortion (AD) and DBT exams associated with patients demonstrating malignant AD, where the dataset includes at least two DBT exams associated with each patient, respectively, where a DBT exam includes a plurality of views; annotating a lesion represented in a circular region-of-interest (ROI) of each of the plurality of views; extracting 3D volumetric samples randomly selected within the ROI of each view; weighting each volumetric sample separately for perilesional and intralesional analysis, with respect to distance from center of the lesion; training an ensemble of DL classifiers to classify the lesion as benign AD or malignant AD, where each member of the ensemble of DL classifiers has a unique combination of lesion view and focus with respect to each other member of the ensemble of DL classifiers; testing each member of the ensemble of DL classifiers on the training set; determining the best performing member of the ensemble of DL classifiers based on the testing of each member of the ensemble of DL classifiers on the training set; and testing the best performing member of the ensemble of DL classifiers on a held out independent validation set.

In one embodiment, the operations further comprise: accessing a diagnostic 3D DBT exam associated with a patient, where the diagnostic 3D DBT exam includes an architectural distortion (AD); providing the diagnostic 3D DBT exam to the best performing member of the ensemble of DL classifiers; and receiving, from the best performing member of the ensemble of DL classifiers, a classification of the AD as a benign AD or as a malignant AD. Embodiments may further include displaying the classification, the diagnostic 3D DBT exam, a member of the plurality of views, or the operating parameters of the ensemble of DL classifiers, on a computer monitor, a smartphone display, a tablet display, or other displays.

Operations, methods, and other embodiments described herein include acquiring electronic data, reading from a computer file, receiving a computer file, reading from a computer memory, or other computerized activity not practically performed in a human mind. For example, accessing a 3D DBT exam, or classifying an AD represented in a 3D DBT exam using an ensemble of DL classifiers, include acquiring electronic data, reading from a computer file, receiving a computer file, reading from a computer memory, or other computerized activity not practically performed in a human mind.

Example 1 is a non-transitory computer-readable medium storing computer-executable instructions that, when executed, cause a processor to perform operations, comprising: accessing one or more medical imaging scans, wherein each medical imaging scan of the one or more medical imaging scans is associated with a distinct angle, wherein each medical imaging scan of the one or more medical imaging scans comprises a segmented region of interest (ROI) of that medical imaging scan comprising a lesion, wherein the segmented ROI of that medical imaging scan comprises one or more regions associated with that lesion; providing a first region of the one or more regions of a first medical imaging scan of the one or more medical imaging scans to a first deep learning (DL) model of an ensemble of DL models and providing a second region of the one or more regions of a second medical imaging scan of the one or more medical imaging scans to a second DL model of the ensemble, wherein the first DL model is trained on the first region and the distinct angle of the first medical imaging scan, wherein the second DL model is trained on the second region and the distinct angle of the second medical imaging scan, and wherein at least one of the first region is different from the second region or the first medical imaging scan is different from the second medical imaging scan; and receiving, from the ensemble of DL models, an indication of whether the lesion is benign or malignant.

Example 2 comprises the subject matter of any variation of any of example(s) 1, wherein the first region is different from the second region and the first medical imaging scan is different from the second medical imaging scan, and wherein the operations further comprise: providing the first region of the second medical imaging scan to a third DL model of the ensemble and providing the second region of the first medical imaging scan to a fourth DL model of the ensemble, wherein the third DL model is trained on the first region and the distinct angle of the second medical imaging scan, and wherein the second DL model is trained on the second region and the distinct angle of the first medical imaging scan.

Example 3 comprises the subject matter of any variation of any of example(s) 1-2, wherein the first region is one of an intralesional region or a perilesional region.

Example 4 comprises the subject matter of any variation of any of example(s) 1-3, wherein the second region is the other of an intralesional region or a perilesional region.

Example 5 comprises the subject matter of any variation of any of example(s) 1-4, wherein the distinct view associated with a first medical imaging scan of the one or more medical imaging scans is one of a craniocaudal (CC) view or a mediolateral (ML) view.

Example 6 comprises the subject matter of any variation of any of example(s) 1-5, wherein the one or more medical imaging scans is two or more medical imaging scans, wherein the distinct view associated with a first medical imaging scan of the two medical imaging scans is a craniocaudal (CC) view, and wherein the distinct view associated with a second medical imaging scan of the two medical imaging scans is a mediolateral (ML) view.

Example 7 comprises the subject matter of any variation of any of example(s) 1-6, wherein the one or more medical imaging scans are one or more 3D Digital Breast Tomosynthesis (DBT) scans.

Example 8 comprises the subject matter of any variation of any of example(s) 1-7, wherein at least one DL model of the ensemble is a convolutional neural network (CNN).

Example 9 comprises the subject matter of any variation of any of example(s) 1-8, wherein the CNN has at least three convolutional layers.

Example 10 comprises the subject matter of any variation of any of example(s) 1-9, wherein at least one DL model of the ensemble has a volumetric kernel.

Example 11 comprises the subject matter of any variation of any of example(s) 1-10, wherein at least one DL model of the ensemble employs one of the following optimizers: an Adam optimizer, a stochastic gradient descent (SGD) optimizer, a SGD optimizer with momentum, or a SGD optimizer with Nesterov momentum.

Example 12 is a non-transitory computer-readable medium storing computer-executable instructions that, when executed, cause a processor to perform operations, comprising: accessing a training set comprising, for each patient of a plurality of patients, one or more medical imaging scans of that patient, wherein each medical imaging scan of the one or more medical imaging scans is associated with a distinct angle, wherein each medical imaging scan of the one or more medical imaging scans of that patient comprises a segmented region of interest (ROI) of that medical imaging scan comprising a lesion of that patient, wherein the segmented ROI of that medical imaging scan comprises a first region of that medical imaging scan associated with the legion of that patient and a second region of that medical imaging scan associated with the lesion of that patient, and wherein the lesion of that patient is associated with a known diagnosis for that patient; for each medical imaging scan of the training set: randomly extracting one or more associated first samples from the first region of that medical imaging scan and one or more associated second samples from the second region of that medical imaging scan; assigning an associated weight to each associated first sample of the one or more associated first samples and to each associated second sample of the one or more associated second samples based at least in part on the known diagnosis for that patient; providing the one or more associated first samples of that medical imaging scan and their associated weights to an associated first Deep Learning (DL) model for the distinct view of that medical imaging scan; providing the one or more associated second samples of that medical imaging scan and their associated weights to an associated second DL model for the distinct view of that medical imaging scan; training the associated first DL model for the distinct view of that medical imaging scan based on the one or more associated first samples of that medical imaging scan and their associated weights; and training the associated second DL model for the distinct view of that medical imaging scan based on the one or more associated second samples of that medical imaging scan and their associated weights; and determining an associated DL model weighting for each DL model of an ensemble of DL models comprising the first DL for the distinct view of each medical imaging scan and the second DL model for the distinct view of each medical imaging scan.

Example 13 comprises the subject matter of any variation of any of example(s) 12, wherein, for each medical imaging scan of the training set, the associated weight assigned to each associated first samples of the one or more associated first samples and to each associated second sample of the one or more associated second samples is based at least in part on a probability defined based on an elliptical segmentation around the associated lesion.

Example 14 comprises the subject matter of any variation of any of example(s) 12-13, wherein the first region is one of an intralesional region or a perilesional region.

Example 15 comprises the subject matter of any variation of any of example(s) 12-14, wherein the second region is the other of an intralesional region or a perilesional region.

Example 16 comprises the subject matter of any variation of any of example(s) 12-15, wherein the distinct view associated with a first medical imaging scan of the training set is one of a craniocaudal (CC) view or a mediolateral (ML) view.

Example 17 comprises the subject matter of any variation of any of example(s) 12-16, wherein the distinct view associated with a first medical imaging scan of the training set is a craniocaudal (CC) view, and wherein the distinct view associated with a second medical imaging scan of the training set is a mediolateral (ML) view.

Example 18 comprises the subject matter of any variation of any of example(s) 12-17, wherein each medical imaging scan of the training set is a 3D Digital Breast Tomosynthesis (DBT) scan.

Example 19 comprises the subject matter of any variation of any of example(s) 12-18, wherein at least one DL model of the ensemble is a convolutional neural network (CNN).

Example 20 comprises the subject matter of any variation of any of example(s) 12-19, wherein the CNN has at least three convolutional layers.

Example 21 comprises the subject matter of any variation of any of example(s) 12-20, wherein at least one DL model of the ensemble has a volumetric kernel.

Example 22 comprises the subject matter of any variation of any of example(s) 12-21, wherein at least one DL model of the ensemble employs one of the following optimizers: an Adam optimizer, a stochastic gradient descent (SGD) optimizer, a SGD optimizer with momentum, or a SGD optimizer with Nesterov momentum.

Example 23 is an apparatus, comprising: a memory configured to store one or more medical imaging scans, wherein each medical imaging scan of the one or more medical imaging scans is associated with a distinct angle, wherein each medical imaging scan of the one or more medical imaging scans comprises a segmented region of interest (ROI) of that medical imaging scan comprising a lesion, wherein the segmented ROI of that medical imaging scan comprises one or more regions associated with that lesion; and one or more processors configured to perform operations comprising: providing a first region of the one or more regions of a first medical imaging scan of the one or more medical imaging scans to a first deep learning (DL) model of an ensemble of DL models and providing a second region of the one or more regions of a second medical imaging scan of the one or more medical imaging scans to a second DL model of the ensemble, wherein the first DL model is trained on the first region and the distinct angle of the first medical imaging scan, wherein the second DL model is trained on the second region and the distinct angle of the second medical imaging scan, and wherein at least one of the first region is different from the second region or the first medical imaging scan is different from the second medical imaging scan; and receiving, from the ensemble of DL models, an indication of whether the lesion is benign or malignant.

Example 24 comprises the subject matter of any variation of any of example(s) 23, wherein the first region is different from the second region and the first medical imaging scan is different from the second medical imaging scan, and wherein the operations further comprise: providing the first region of the second medical imaging scan to a third DL model of the ensemble and providing the second region of the first medical imaging scan to a fourth DL model of the ensemble, wherein the third DL model is trained on the first region and the distinct angle of the second medical imaging scan, and wherein the second DL model is trained on the second region and the distinct angle of the first medical imaging scan.

Example 25 comprises the subject matter of any variation of any of example(s) 23-24, wherein the first region is one of an intralesional region or a perilesional region.

Example 26 comprises the subject matter of any variation of any of example(s) 23-25, wherein the second region is the other of an intralesional region or a perilesional region.

Example 27 comprises an apparatus comprising means for executing any of the described operations of examples 1-26.

Example 28 comprises a machine readable medium that stores instructions for execution by a processor to perform any of the described operations of examples 1-26.

Example 29 comprises an apparatus comprising: a memory; and one or more processors configured to: perform any of the described operations of examples 1-26.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:

accessing one or more medical imaging scans, wherein the one or more medical imaging scans comprise a first medical imaging scan associated with a first distinct angle and a second medical imaging scan associated with a second distinct angle, wherein each medical imaging scan of the one or more medical imaging scans comprises a segmented region of interest (ROI) comprising a first region and a second region associated with a lesion;

applying different weights to the first region and the second region of the first medical imaging scan and the second medical imaging scan to form a first weighted region and a second weighted region, wherein the different weights are based upon spatial positions of the first region and the second region and wherein the different weights comprise a probabilistic weighting determined from probability distributions representing the first region and the second region within the first medical imaging scan and the second medical imaging scan;

providing the first weighted region of the first medical imaging scan to a first deep learning (DL) model of an ensemble of DL models and providing the second weighted region of the second medical imaging scan to a second DL model of the ensemble, wherein the first DL model is operated on the first weighted region and the second DL model is operated on the second weighted region, and wherein at least one of the first region is different from the second region or the first medical imaging scan is different from the second medical imaging scan; and receiving, from the ensemble of DL models, an indication of whether the lesion is benign or malignant.

2. The non-transitory computer-readable medium of claim 1, wherein the first region and the second region are taken from an architectural distortion having a spiculated mass and radiating lines, and wherein the first region is closer to a boundary between the spiculated mass and the radiating lines than the second region, the first region being assigned a lower weight than the second region.

3. The non-transitory computer-readable medium of claim 1, wherein the first region is one of an intralesional region or a perilesional region.

4. The non-transitory computer-readable medium of claim 3, wherein the second region is the other of the intralesional region or the perilesional region.

5. The non-transitory computer-readable medium of claim 1, wherein a distinct view associated with the first medical imaging scan of the one or more medical imaging scans is one of a craniocaudal (CC) view or a mediolateral (ML) view.

6. The non-transitory computer-readable medium of claim 1, wherein the one or more medical imaging scans is two or more medical imaging scans, wherein a distinct view associated with the first medical imaging scan of the two or more medical imaging scans is a craniocaudal (CC) view, and wherein a distinct view associated with the second medical imaging scan of the two or more medical imaging scans is a mediolateral (ML) view.

7. The non-transitory computer-readable medium of claim 1, wherein the one or more medical imaging scans are one or more 3D Digital Breast Tomosynthesis (DBT) scans.

8. The non-transitory computer-readable medium of claim 1, wherein at least one DL model of the ensemble is a convolutional neural network (CNN).

9. The non-transitory computer-readable medium of claim 1, wherein the probability distributions are Gaussian distributions.

10. The non-transitory computer-readable medium of claim 1, wherein at least one DL model of the ensemble has a volumetric kernel.

11. The non-transitory computer-readable medium of claim 1, wherein at least one DL model of the ensemble employs one of the following optimizers: an Adam optimizer, a stochastic gradient descent (SGD) optimizer, a SGD optimizer with momentum, or a SGD optimizer with Nesterov momentum.

12. A non-transitory computer-readable medium storing computer-executable instructions that, when executed, cause a processor to perform operations, comprising:

accessing a training set comprising, for each patient of a plurality of patients, one or more medical imaging scans of that patient, wherein each medical imaging scan of the one or more medical imaging scans is associated with a distinct angle, wherein each medical imaging scan of the one or more medical imaging scans of that patient comprises a segmented region of interest (ROI) including a first region of that medical imaging scan associated with a lesion of that patient and a second region of that medical imaging scan associated with the lesion of that patient;

for each medical imaging scan of the training set:
extracting one or more associated first samples from the first region of that medical imaging scan and one or more associated second samples from the second region of that medical imaging scan;
assigning an associated weight to each associated first sample of the one or more associated first samples and to each associated second sample of the one or more associated second samples, the associated weight is based upon spatial positions of the associated first sample and the associated second sample and comprises a probabilistic weight determined from probability distributions representing the first region and the second region;
training an associated first Deep Learning (DL) model for a distinct view of that medical imaging scan based on the one or more associated first samples of that medical imaging scan and their associated weights; and
training an associated second DL model for a distinct view of that medical imaging scan based on the one or more associated second samples of that medical imaging scan and their associated weights; and determining an associated DL model weighting for each DL model of an ensemble of DL models comprising the first DL for the distinct view of each medical imaging scan and the second DL model for the distinct view of each medical imaging scan.

13. The non-transitory computer-readable medium of claim 12, wherein, for each medical imaging scan of the training set, the associated weight assigned to each associated first sample of the one or more associated first samples and to each associated second sample of the one or more associated second samples is based at least in part on a probability defined based on an elliptical segmentation around the associated lesion.

14. The non-transitory computer-readable medium of claim 12, wherein the first region is one of an intralesional region or a perilesional region.

15. The non-transitory computer-readable medium of claim 14, wherein the second region is the other of the intralesional region or the perilesional region.

16. The non-transitory computer-readable medium of claim 12, wherein the distinct view associated with a first medical imaging scan of the training set is one of a craniocaudal (CC) view or a mediolateral (ML) view.

17. The non-transitory computer-readable medium of claim 12, wherein the distinct view associated with a first medical imaging scan of the training set is a craniocaudal (CC) view, and wherein the distinct view associated with a second medical imaging scan of the training set is a mediolateral (ML) view.

18. The non-transitory computer-readable medium of claim 12, wherein each medical imaging scan of the training set is a 3D Digital Breast Tomosynthesis (DBT) scan.

19. The non-transitory computer-readable medium of claim 12, wherein at least one DL model of the ensemble is a convolutional neural network (CNN).

20. The non-transitory computer-readable medium of claim 12, wherein the probability distributions are Gaussian distributions.

21. The non-transitory computer-readable medium of claim 12, wherein at least one DL model of the ensemble has a volumetric kernel.

22. The non-transitory computer-readable medium of claim 12, wherein at least one DL model of the ensemble employs one of the following optimizers: an Adam optimizer, a stochastic gradient descent (SGD) optimizer, a SGD optimizer with momentum, or a SGD optimizer with Nesterov momentum.

23. An apparatus, comprising:
- a memory configured to store one or more medical imaging scans, wherein each medical imaging scan of the one or more medical imaging scans is associated with a distinct angle, wherein each medical imaging scan of the one or more medical imaging scans comprises a segmented region of interest (ROI) comprising one or more regions associated with an architectural distortion; and
- one or more processors configured to perform operations comprising:
  - applying different probabilistic weights to the one or more regions of the one or more medical image scans, wherein the different probabilistic weights are determined from probability distributions representing the one or more regions;
  - providing a first region of the one or more regions of a first medical imaging scan of the one or more medical imaging scans to a first deep learning (DL) model of an ensemble of DL models and providing a second region of the one or more regions of a second medical imaging scan of the one or more medical imaging scans to a second DL model of the ensemble, wherein the first DL model is trained on the first region and the distinct angle of the first medical imaging scan, wherein the second DL model is trained on the second region and the distinct angle of the second medical imaging scan, and wherein at least one of the first region is different from the second region or the first medical imaging scan is different from the second medical imaging scan; and
  - receiving, from the ensemble of DL models, an indication of whether the architectural distortion is benign or malignant.

24. The apparatus of claim 23, wherein the architectural distortion comprises a lesion.

25. The apparatus of claim 23, wherein the different probabilistic weights are based upon spatial positions of the one or more regions.

26. The apparatus of claim 23, wherein the probability distributions are Gaussian distributions.

* * * * *